US00PP13723P29

(12) United States Plant Patent
Danziger

(10) Patent No.: US PP13,723 P2
(45) Date of Patent: Apr. 15, 2003

(54) TORENIA PLANT NAMED 'DANTOPUR'

(75) Inventor: Gabriel Danziger, Nir-Zvi (IL)

(73) Assignee: Danziger - "DAN" Flower Farm, Moshav Mishmar Hashiva (IL)

( * ) Notice: Subject to any disclaimer, the term of this patent is extended or adjusted under 35 U.S.C. 154(b) by 0 days.

(21) Appl. No.: 09/984,771

(22) Filed: Oct. 31, 2001

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—Foley & Lardner

(57) ABSTRACT

A new and distinct Torenia plant named 'Dantopur' characterized by having a 80–100 cm. spread in diameter, trailing vigorous growth, densely branched plant, gracefully cascading from hanging baskets; shiny green foliage, plenty of delicate, funnel shaped flowers in shades of violet-blue with a distinct yellow spot; growth at a moderate temperature range of 10–25° C.; early, year round flowering, except for middle of winter.

2 Drawing Sheets

Latin name of the genus and species of the plant claimed: *Scorphulriacea Torenia hybrida.*

Variety denomination: 'Dantopur'; commercial: Torenia Purple Moon.

BACKGROUND OF THE INVENTION

The present invention relates to a new and distinct cultivar of Torenia plant, hereinafter referred to by the cultivar name 'Dantopur'.

The new cultivar was originated from a cross made in a controlled breeding program in Moshav Mishmar Hashiva, Israel. 'Dantopur' was discovered and selected by the inventor, Gabriel Danziger, as a flowering plant within the progeny of the stated cross in a controlled environment in Moshav Mishmar Hashiva, Israel. The male parent is Torenia 'Clown Mix' (unpatented), and the female parent is Torenia 'Dantoyhrt' (U.S. Plant Pat. No. 11,784).

Asexual reproduction of the new cultivar by vegetative cuttings, was first preformed in August 2000, in Mismar Hashiva, Israel and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be basic characteristics of 'Dantopur' which in combination distinguish this Torenia as a new and distinct cultivar:

1. Funnel shaped violet-blue flowers with a distinctive yellow spot;
2. 80–100 cm plant spread, densely branched;
3. Trailing vigorous growth;
4. Shiny green foliage
5. Early, year round flowering, except for middle winter;
6. Growth at a moderate temperature range of 10–25° C.
7. For use as hanging pots, outdoors under partial shade.

'Dantopur' has not been observed under all possible environmental conditions. The phenotype of the new cultivar may vary significantly with variations in environment such as temperature, light intensity, and day length without any change in the genotype of the plant. The following observations, measurements and values describe the new cultivar as grown in Moshav Mishmar Hashiva, Israel under conditions which closely approximate those generally used in commercial practice.

Of the many commercial cultivars known to the present inventor, the most similar in comparison to 'Dantopur' is the cultivar 'Dantoyhrt', commerically known as Torenia 'Yellow Heart Moon' (U.S. Plant Pat. No. 11,784). While 'Dantoyhrt' is a taller plant, 15 cm in contrast to the height of 'Dantopur' at 5–10 cm, 'Dantopur' has a larger spread of 80–100 cm in comparison to the spreading area of 'Dantoyhrt' at 60 cm. The petal color of 'Dantoyhrt' varies from the petal color of 'Dantopur'. The top petal of 'Dantoyhrt' is uniformly light violet-blue RHS 91-A, with the margins darkening to RHS 92-A with age; side petals are RHS 89-B, lower petal yellow spot is RHS 2-A, encircled by RHS 93-B, followed by RHS 91-A, finishing with RHS 93-B. In contrast, the top petal of 'Dantopur' is dark violet-blue RHS 93-A, and light violet blue RHS 96-D toward the base; side petals are RHS 89-A; the lower petal yellow spot is RHS 2-A encircled by RHS 96-D, followed by RHS 93-A, and finishing toward the margin with violet-blue RHS 89-A. cl

BRIEF DESCRIPTION OF THE DRAWING

The accompanying photographic drawings show a typical plant of 'Dantopur' with colors as true as possible with drawings of this type.

The first drawing shows a flowering plant of 'Dantopur'.

The second drawing shows a comparison of 'Dantopur', as grown in partial shade, to Torenia 'Yellow Heart Moon'.

DETAILED BOTANICAL DESCRIPTION

The following observations, measurements and values describe the new cultivar as grown in Moshav Mishmar Hashiva, Israel under conditions which closely approximate those generally used in commercial practice. Color references are made to The Royal Horticultural Society Colour Chart (R.H.S.), except where general colors of ordinary significance are used. Color values were taken under daylight conditions at approximately 12:00 P.M. in Moshav Mishmar Hashiva, Israel.

Parentage:
*Male parent*.—Torenia 'Clown Mix'.
*Female parent*.—Torenia 'Dantoyhrt'.
Propagation: Tissue culture and soft tip cuttings.
Plant:
*Form*.—Spreading.
*Height*.—5–10 cm.
*Spreading area*.—80–100 cm. in diameter.
*Blooming period*.—Year round except for middle winter.
*Cold tolerance*.—>10° C.
*Plant vigor*.—30 cm. per month.
*Optimal growth*.—Growth at a moderate temperature range of 10–25° C.; fertilize constantly; irrigate once daily, more in hot weather; best performance in partial shade.
Stem:
*Color*.—Yellow-Green RHS 144-C.
*Diameter*.—3 mm.
*Pubescence*.—Few.
*Branching*.—Many.
*Length of internodes*.—5–9 cm.
Foliage:
*Overall shape*.—Oval.
*Base*.—Obovate.
*Tip*.—Acuminate.
*Margin*.—Serrate.
*Color*.—Center color of leaf: Shiny green RHS 143-A. Upper side: Shiny green RHS 143-A. Under side: Shiny green RHS 143-C.
*Size of leaf*.—Width: 3 cm. Length: 4.5 cm.
*Petioles*.—5–7 mm, green RHS 143-A.
*Leaf surface*.—Convex.
*Veination*.—None.
Flowers:
*Blooming period*.—Year round except for middle of winter.
*Flowering stem*.—None. Flowers appear along the growing stems.
*Orientation at opening*.—Slanting upward.
*Type*.—Single.
*Shape*.—Funnelform.
Petals:
*Size*.—3.5 cm wide, 4 cm long.
*Shape*.—Funnelform.
*Color*.—Upper side: The top petal is dark violet-blue RHS 93-A, and light violet blue RHS 96-D toward the base. The two side petals are a violet-blue RHS 89-A. The lower petal consists of 4 color zones: an inner zone (spot) of yellow RHS 2-A, encircled by a zone of light violet-blue RHS 96-D, followed by a zone of dark violet blue RHS 93 A, and finishing towards the margin with violet-blue RHS 89-A. Under side: Top petal violet-blue RHS 96-A with RHS 95-B towards the edge of the petal, side petals RHS 95-A, lower petal yellow RHS 8-B, encircled by a zone of light violet-blue RHS 97-A, followed by violet-blue RHS 96-A. Throat: Upper surface RHS 1-B, under side RHS 97-A.
*Peduncle*.—Length: 2.5–3 cm.
Bud:
*Shape*.—Elliposidal.
*Size*.—Length: 1.5 cm. Diameter: 8–9 mm.
*Color*.—Green RHS 143-B.
Reproductive organs:
*Stamen*.—Number: 4. Color: Violet-Blue RHS 92-D.
*Style*.—Color: Violet-Blue RHS 92-D.
*Anther*.—Color: Violet-Blue RHS 94-A.
*Filament*.—Color: Violet-Blue RHS 92-D.
*Ovaries*.—Number: 1. Color: Green RHS 143-C.
Seed/fruit: None.
Pest/disease resistance and/or susceptibility: A standard preventive spray program is sufficient as no susceptibility was observed.

I claim:
1. A new and distinct Torenia plant named 'Dantopur', substantially as illustrated and described herein.

* * * * *

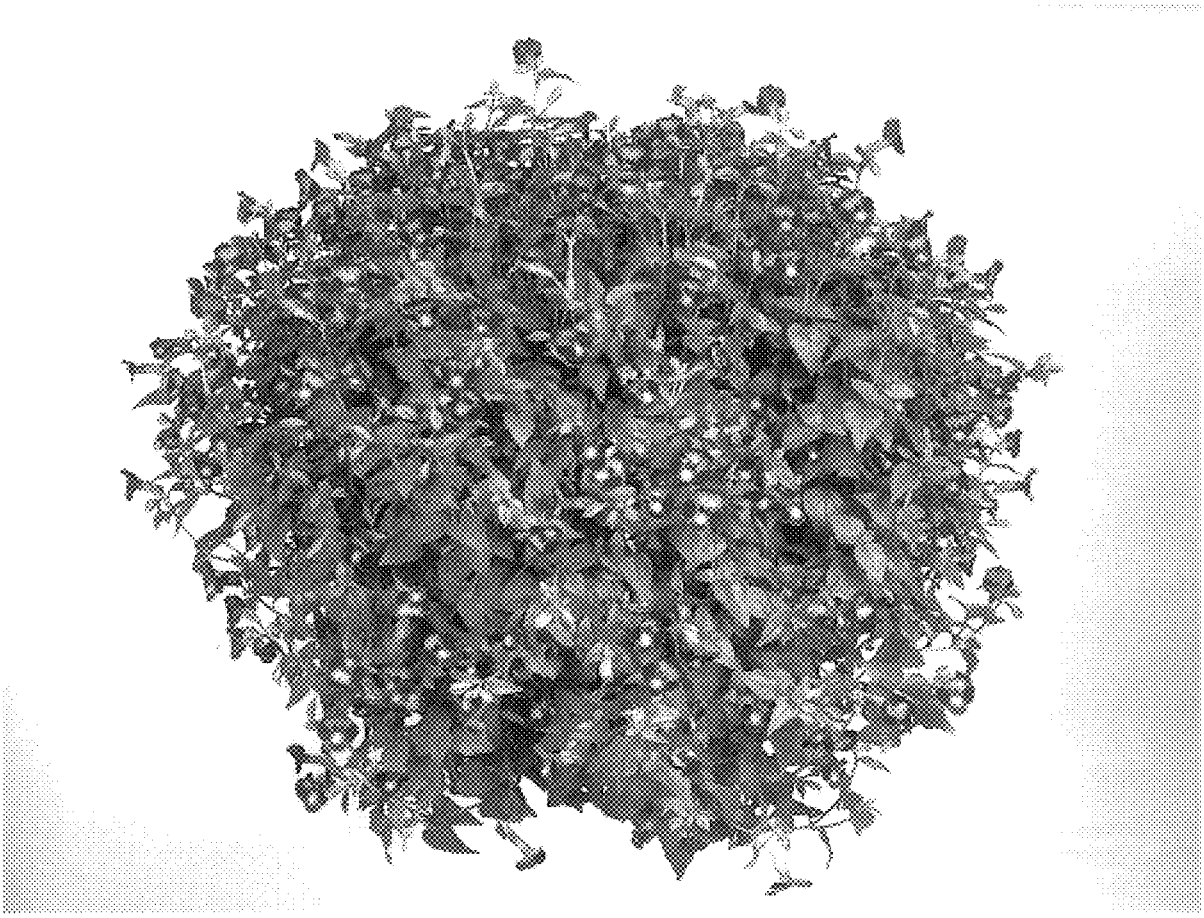

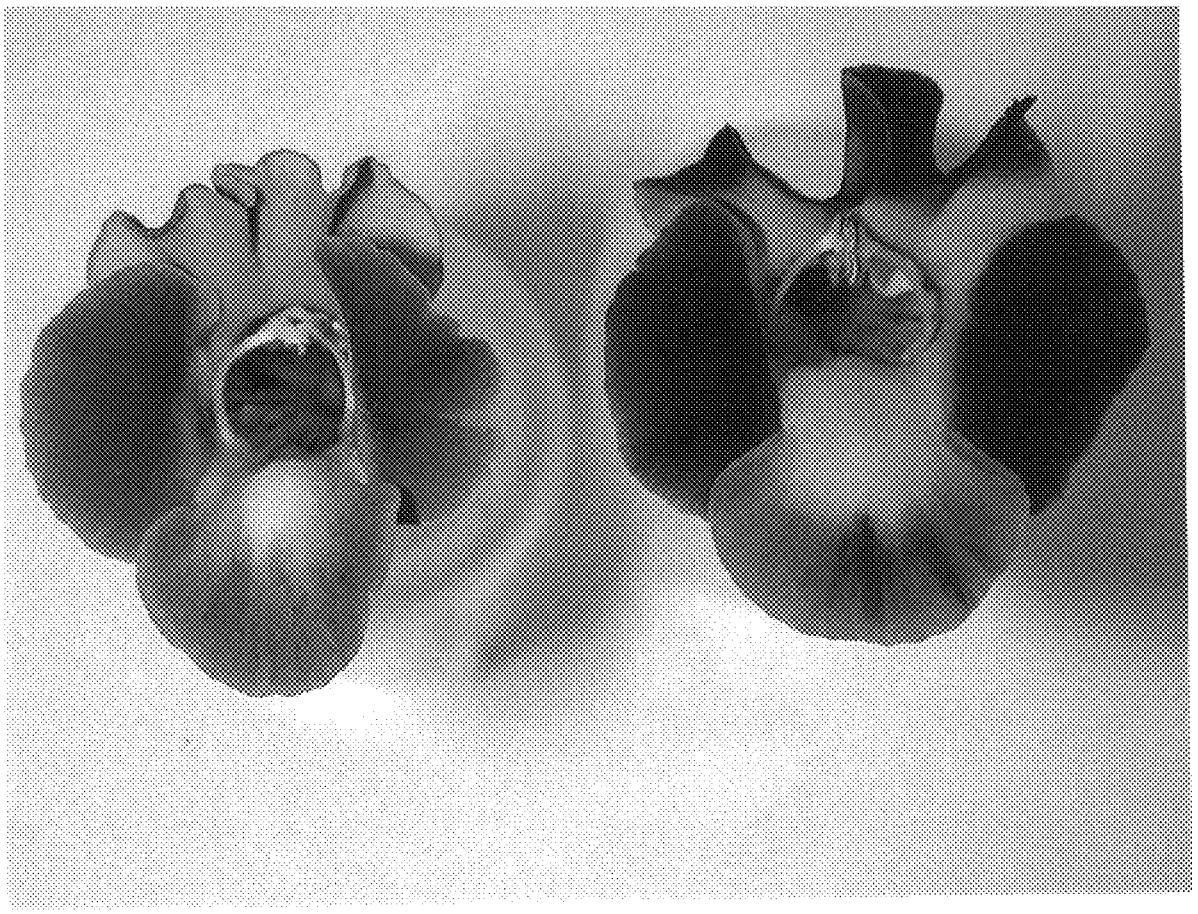
YELLOW HEART MOON
DANTOPUR'